United States Patent [19]

Fain

[11] Patent Number: 5,531,767

[45] Date of Patent: Jul. 2, 1996

[54] METHOD AND APPARATUS FOR DELIVERING DEFIBRILLATION SHOCKS WITH IMPROVED EFFECTIVENESS

[75] Inventor: Eric S. Fain, Menlo Park, Calif.

[73] Assignee: Ventritex, Inc., Sunnyvale, Calif.

[21] Appl. No.: 450,168

[22] Filed: May 25, 1995

Related U.S. Application Data

[62] Division of Ser. No. 219,605, Mar. 29, 1994, Pat. No. 5,500,008.

[51] Int. Cl.$^6$ ........................................ A61N 1/39
[52] U.S. Cl. ............................................... 607/5
[58] Field of Search ................................. 607/5, 7

[56] References Cited

U.S. PATENT DOCUMENTS

| | | | |
|---|---|---|---|
| 3,612,041 | 10/1971 | Ragsdale | 128/2.06 A |
| 3,614,954 | 10/1971 | Mirowski et al. | 128/419 |
| 3,698,386 | 10/1972 | Fried | 128/2.06 A |
| 4,114,628 | 9/1978 | Rizk | 128/419 |
| 4,523,959 | 6/1985 | Zibell | 128/419 |
| 4,825,871 | 5/1989 | Cansell | 128/419 |
| 5,107,834 | 4/1992 | Ideker et al. | 128/419 |
| 5,107,850 | 4/1992 | Olive | 128/705 |
| 5,184,615 | 2/1993 | Nappholz et al. | 128/419 |
| 5,188,105 | 2/1993 | Keimel | 128/419 |
| 5,190,034 | 3/1993 | Sholder | 128/419 |
| 5,193,550 | 3/1993 | Duffin | 128/697 |
| 5,205,283 | 4/1993 | Olson | 128/419 |
| 5,265,602 | 11/1993 | Anderson et al. | 128/419 |
| 5,331,966 | 7/1994 | Bennett et al. | 128/696 |

OTHER PUBLICATIONS

"Ventricular Fibrillation: The Importance of Being Coarse?", Jones, et al., J. Electrocardiology 17 (4), 1984, 393–400.

"Synchronization of Low–Energy Pulses to Rapid Deflection Signals as a Possible Mechanism of Subthreshold Ventricular Defibrillation", Mower, et al., Am. Heart Assoc. Abstracts of 55th Scientific Sessions, No. 298.

"Wavefront Orientation Effects on Bipolar Epicardial Electrograms", Blanchard, et al., Computers in Cardiology, Sep. 23–26, 1990 (IEEE 1991), pp. 111–114).

"Genesis of Sigmoidal Dose–Response Curve During Defibrillation by Random Shock: A Theoretical Model Based on Experimental Evidence for a Vulnerable Window During Ventricular Fibrillation", Hsai, et al., PACE, vol. 13, Oct. 1990, pp. 1326–1342.

"On–Line Electronic Identification of a Period of Vulnerability to Defibrillation using Real–Time Ventricular Fibrillation Waveform Aanlsys", Hsai, et al., pp. 0267.

"Fourier Analysis of Ventricular Fibrillation and Synchronization of DC Countershocks in Defibrillation", Carlisle, et al., Journal of Electrocardiology, 21 (4) 1988, pp. 337–343.

*Primary Examiner*—William E. Kamm
*Attorney, Agent, or Firm*—Steven M. Mitchell; Mark J. Meltzer

[57] ABSTRACT

A method for defibrillating a patient's heart with an implantable defibrillator having defibrillation synchronized to the fibrillation waveform is disclosed. The defibrillator is used to detect fibrillation in a patient's heart, monitor at least one far-field fibrillation voltage across two spaced-apart electrodes while the high voltage capacitors are charging, then deliver a high energy shock during a period of ventricular fibrillation when the absolute values of the peak and trough voltages exceed a threshold based on a desired percentage greater than a running average of the absolute values of the peaks and troughs of the fibrillation voltages monitored during and after capacitor charging. The shock is then delivered synchronous with the next significant cardiac complex. The defibrillator also includes a safety timer so that if the threshold is not reached within a specified safe time limit, the high energy shock will be delivered without further delay.

15 Claims, 5 Drawing Sheets

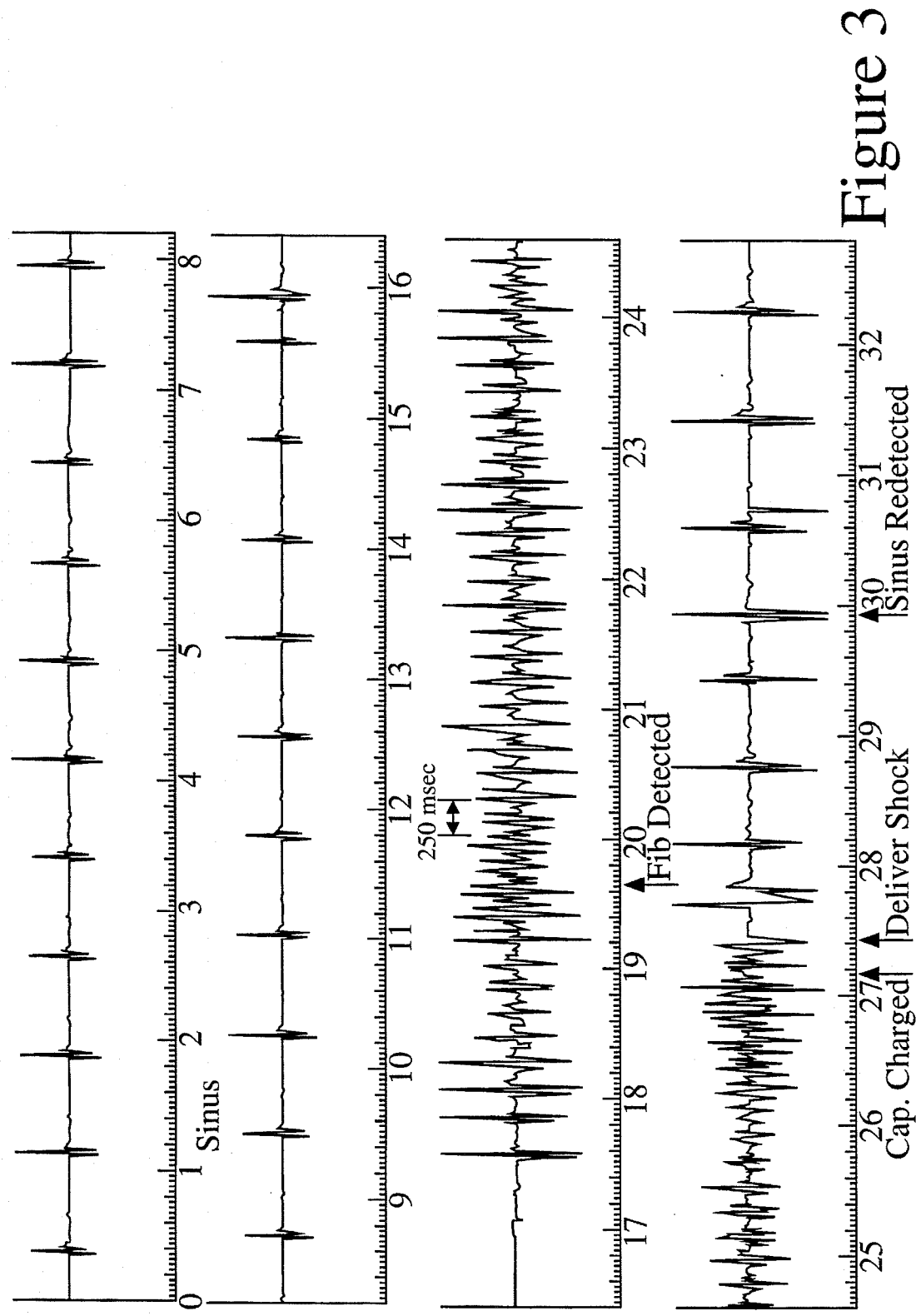

METHOD AND APPARATUS FOR DELIVERING DEFIBRILLATION SHOCKS WITH IMPROVED EFFECTIVENESS

This is a division of application Ser. No. 08/219,605, filed on Mar. 29, 1994, now U.S. Pat. No. 5,500,008.

FIELD OF THE INVENTION

The present invention relates generally to implantable cardiac stimulation devices, and more specifically to an implantable defibrillator that delivers defibrillation energy synchronously with the fibrillation waveform.

BACKGROUND OF THE INVENTION

Following detection of ventricular fibrillation, prior art implantable defibrillators typically deliver a defibrillation shock as soon as their high voltage (HV) capacitors are charged, and in more advanced systems, after ventricular fibrillation (VF) is reconfirmed. The timing of the shock is either not related to the status of the VF signal or is delivered synchronous with the next cardiac complex after reconfirmation and/or charge completion.

In "Genesis of Sigmoidal Dose-Response Curve During Defibrillation by Random Shock: A Theoretical Model Based on Experimental Evidence for a Vulnerable Window During Ventricular Fibrillation," in *PACE* 1990, 13:1326–1342, Hsia and Mahmud discuss a theoretical model and experimental results for using a surface electrocardiogram (ECG) to identify a window of VF during which the heart is more susceptible to defibrillation. In their experiments, they compared the VF waveform voltage at the time of shock delivery for successful and unsuccessful shocks. The shock strength was held constant, and was chosen to produce a defibrillation success rate of 50%. When using a recording from a lead II surface ECG, the absolute VF voltage (AVFV) was found to exhibit significantly larger values for successful defibrillation as compared to unsuccessful defibrillation. However, their experiments using intracardiac electrograms from two epicardial patch electrodes instead of a lead II ECG to track the state of VF showed no significant difference in AVFV between successful and unsuccessful defibrillation. They do not disclose how using the window of VF susceptible to defibrillation could be used in an implantable device.

In an abstract from an American Heart Association conference in Atlanta, November 1993, Hsia and Frerk et al. describe "On-line Electronic Identification of a Period of Vulnerability to Defibrillation using Real-Time Ventricular Fibrillation Waveform Analysis". If implemented as described, however, this system would not work in a conventional implantable device because the electrogram from a bipolar pair of endocardial pacing and sensing electrodes would not provide the information necessary to generate a useful AVFV, which is needed to determine the window of susceptibility to defibrillation.

SUMMARY OF THE INVENTION

The implantable defibrillator of the present invention reduces the defibrillation threshold (DFT) by delivering a defibrillation shock during a period of ventricular fibrillation (VF) when the heart is most susceptible to defibrillation. Variation in the state of excitability of cardiac tissue results in a cyclic period of increased susceptibility to defibrillation. The susceptible period occurs at a time when the number of excitable cells is low, i.e., a higher state of total depolarization. Far-field sensing is used to provide an electrogram that is monitored during VF, beginning with charging of the high voltage capacitors, to determine a relative measure of the absolute ventricular fibrillation voltage (AVFV), which is a crude marker of the number of excitable cells. Because an electrogram is sensitive to the location of the sensing electrodes, it is important to use unipolar, i.e. far-field, sensing to find the higher state of total depolarization in the heart. A bipolar signal, which is the usual signal used for sensing in implantable defibrillators, gives information regarding only the VF wavefronts passing through the localized area between the two electrodes, typically the RV pacing and RV sensing electrodes. The amplitude of the signal depends, in part, on the direction the wavefront is traveling; the signal will be largest when traveling parallel to the two electrodes, and smallest when perpendicular to them. By using electrodes that are at least 4 centimeters apart, a more global ventricular fibrillation signal is obtained. This signal is continually monitored, usually beginning with charging of the high voltage capacitors. In the preferred embodiment, a running average of the AVFV, for example the last 5 seconds, is utilized to determine whether the ECG signal is relatively large or small. When the capacitors are fully charged, the shock is delivered during a period of VF when the absolute values of the peak and trough voltages, calculated within a successive series of 250 msec windows exceed the calculated average monitored during the running window by a desired amount, for example 125%. The running average is calculated by looking at a predetermined number of the most recent 250 msec windows, typically 5 seconds or about 20 windows. The value of each window may be calculated by averaging the absolute value of all the data points in a window, averaging the absolute values of all the peaks and troughs in a window or looking at the area under the curve for the window. In the preferred embodiment only the most recent signal is considered since older data may not be relevant in determining when to deliver the defibrillation shock. The defibrillation shock is timed to coincide with a relative maximum absolute VF voltage (a peak or a trough).

In an alternative embodiment, a relative maximum amplitude of the absolute VF voltages from the windows is calculated and a shock is delivered upon the completion of charging of the high voltage capacitors and reconfirmation of VF when the measured AVFV is within a desired percentile of the relative maximum, for example 50 to 90%. As with the running average, the number of windows used to determine the relative maximum is limited to the most recent time period, for example 5 seconds. This ensures that only the most relevant portion of the VF signal is used to determine when to deliver the defibrillation shock.

More than two electrodes may be used in combination to generate the VF signal or signals. Two pairs of electrodes may be used, with or without one electrode in common, to observe fibrillation wavefronts from two directions.

The electrodes used for VF monitoring may be the same electrodes used to deliver the high energy defibrillation shock and provide pacing and sensing. This is advantageous since no extra leads are required, and the present invention can be used with existing lead systems.

A safety timer is included in the defibrillator so that if a relatively large absolute VF voltage is not obtained to trigger delivery of the shock within a certain time, say 5 seconds from the completion of charging of the high voltage capacitors and reconfirmation of VF, the shock will be delivered. The shock will still be delivered synchronous with the next cardiac complex. Note that the safety timer could alternatively be set to time from the detection of initiation of VF.

The present invention is directed toward the provision of a defibrillator that increases the likelihood for successful defibrillation at any particular shock strength by delivering the defibrillation pulse during a period corresponding to a relatively high state of depolarization of the heart cells as monitored by a unipolar electrogram during VF.

It is thus a primary object of this invention to provide an implantable cardiac defibrillator that delivers a defibrillation pulse at a time most likely to defibrillate the heart.

It is a further object of this invention to provide an implantable cardiac stimulation system that can be used with previously implanted defibrillation lead systems.

BRIEF DESCRIPTION OF THE DRAWINGS

The various features and advantages of the present invention may be more readily understood with reference to the following detailed description taken in conjunction with the accompanying drawings in which:

FIG. 3 is a simulated recording of a far-field electrogram recording during ventricular fibrillation and showing delivery of a defibrillation shock.

DETAILED DESCRIPTION OF THE INVENTION

The present invention is directed toward the provision of a defibrillator that delivers a defibrillation shock to the heart during a period of ventricular fibrillation (VF) in which the shock is likely to be successful in defibrillating the heart. Variation in the state of excitability of the cells in the heart results in a cyclic period of increased susceptibility to defibrillation. The susceptible period occurs when the number of excitable cells is low, i.e., a higher state of total depolarization. The absolute VF voltage (AVFV) is a crude marker of the number of excitable cells.

Figure 1:
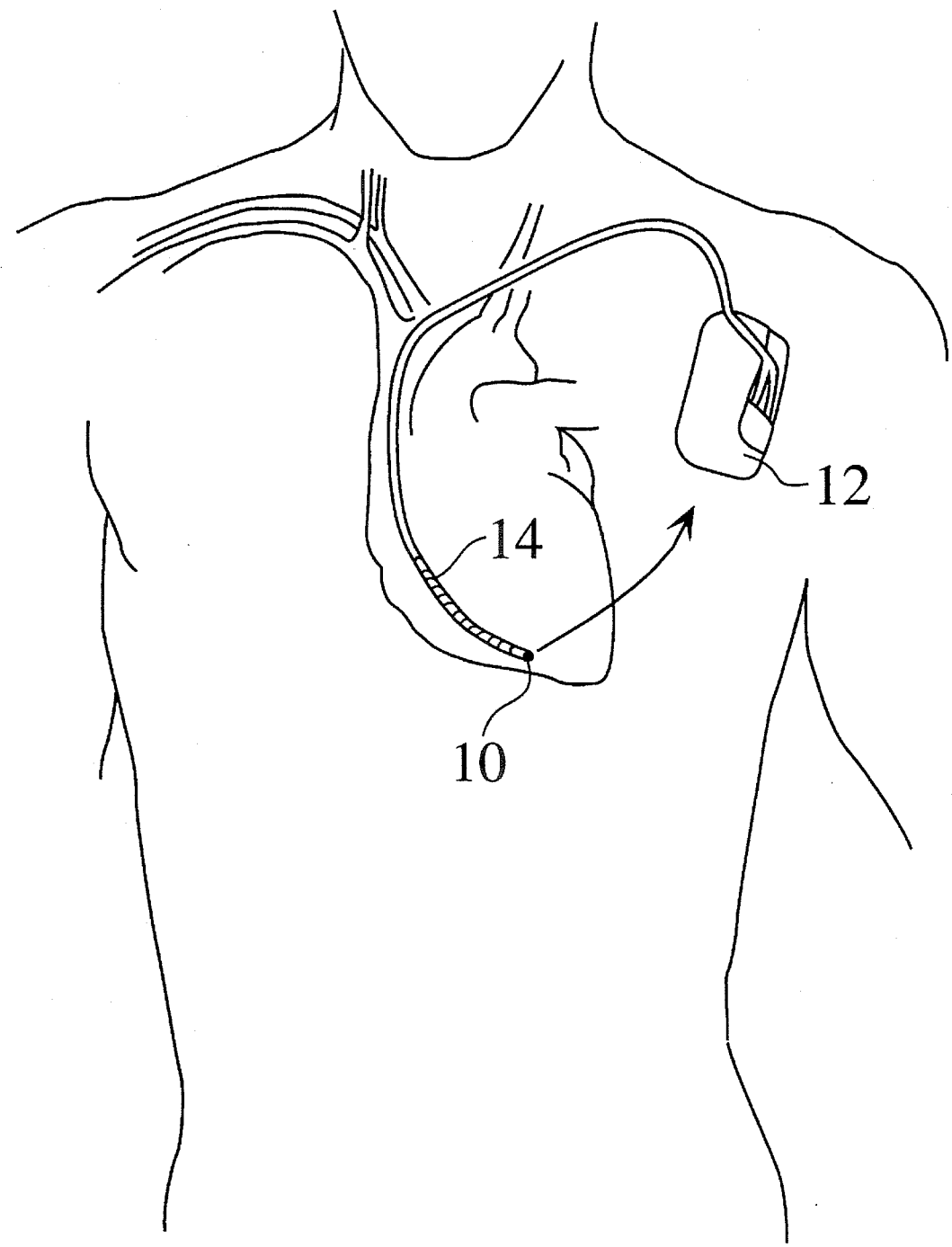
FIG. 1 is an illustration of a right ventricular (RV) pacing electrode and an active pulse generator case placed subcutaneously (SubQ) in the patient's left pectoral region used to sense the far-field ventricular electrogram.

FIG. 1 is an illustration of a right ventricular (RV) pacing electrode 10 and an active pulse generator case 12 located subcutaneously (SubQ) in the patient's left pectoral region for sensing the far-field ventricular electrogram. Unlike the bipolar electrogram that would be obtained by sensing from the RV pacing electrode 10 to the RV sensing and/or defibrillation electrode 14 (the usual combination for sensing), the far-field, or unipolar, electrogram provides the necessary information to determine the period of increased susceptibility to defibrillation. A conventional bipolar sensor may also be used to provide ECG signals to the fibrillation detection circuitry.

Figure 2A:
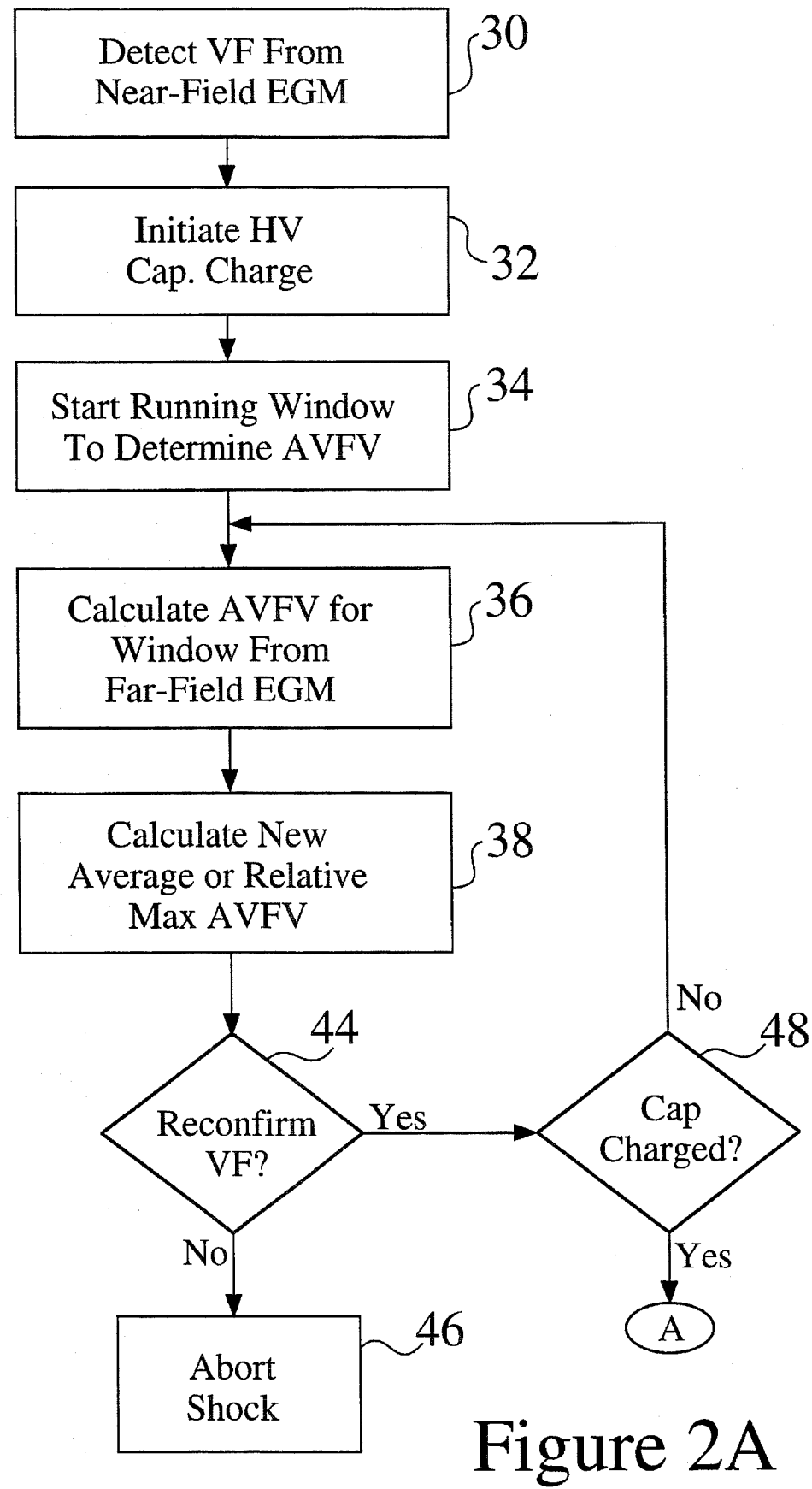
FIGS. 2A and 2B are a flow diagram illustrating the processing of electrograms in order to deliver defibrillation energy when the heart is most susceptible to being defibrillated.
Figure 2B:
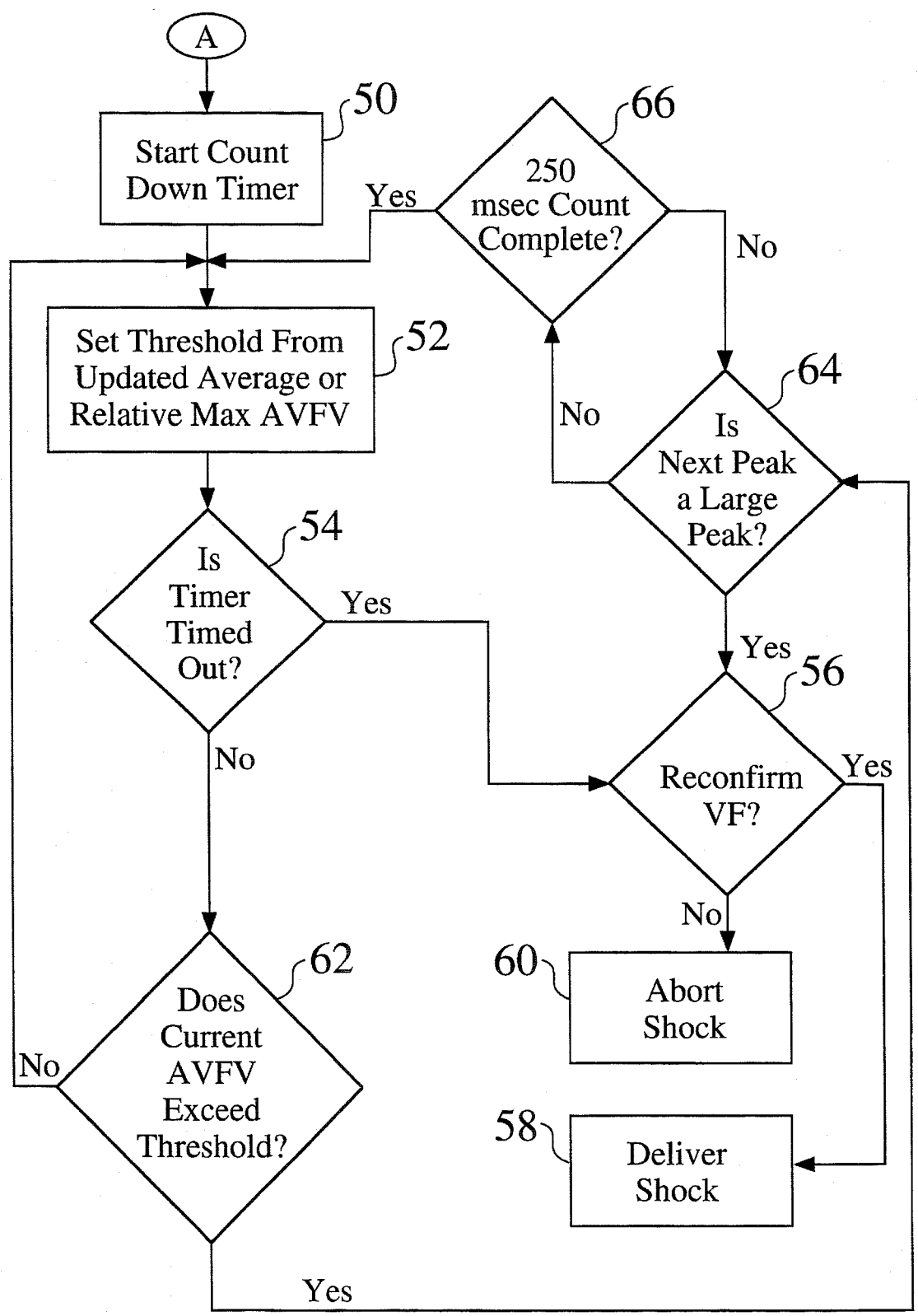

FIGS. 2A and 2B are a flow diagram of the steps performed by the logic and detection circuitry of the implantable defibrillator for processing the near-field and far-field ventricular electrograms in order to deliver defibrillation energy when the heart is most susceptible to being defibrillated. A fibrillation of the patient's heart is detected at step 30 using conventional detection techniques and a near-field electrogram. Charging of the high voltage (HV) capacitors is started at step 32 following VF detection. A running sequence of windows is started at step 34 to determine the AVFV for the far-field electrogram during capacitor charging. In the preferred embodiment, the running sequence of windows is about 5 seconds long but it could be longer or shorter. A series of smaller windows, each window in the sequence is about 250 msec long. Only the most recent windows comprising the sequence are used for calculations in setting the threshold to be discussed below. It should be noted that the sequence of windows, which is chosen to have a time long enough to optimally characterize the signal strength or identify a local relative maximum signal, does not have a physical existence but is a continuing calculation of a most recent fixed period of the electrogram signal. In the preferred embodiment, a new window is calculated every 250 msec, thus providing a sequence of slices along the data signal. Alternatively, a new window could be calculated with each new data point so that the window slides along the data signal. With either method, it is preferred that only the most recent portion of the VF data signal be used to calculate a running average or a relative maximum of the AVFV. The AVFV during each window can be calculated in a number of ways including taking an average of the absolute value of all detected points, taking an average of the absolute value of all peaks, or making an area under the waveform curve calculation or using other comparable algorithms. To facilitate this calculation, it is preferred that the detected ECG be digitized early in the processing as is shown in U.S. Pat. No. 5,027,814 to Carroll et al., which patent is incorporated herein by reference.

At this point, a loop is started which lasts during the charging of the HV capacitors. An AVFV is calculated for each new window at step 36 using the far-field EGM. A new average or relative maximum AVFV is then calculated at step 38 with each new window in the sequence. For the calculation of the relative maximum, each time a new value is generated, all the values in the running window are compared and the largest becomes the new relative maximum. The presence of ventricular fibrillation is reconfirmed as step 44. If VF is not still present, the shock is aborted at step 46 and charging of the capacitors is halted. If the VF is still present and the capacitors are not fully charged, step 48 causes the system to loop back to step 38 to calculate the next AVFV of the running sequence of windows.

Referring now to FIG. 2B, once the HV capacitors are fully charged, as a safety measure, a count down timer is started at step 50. Next, an AVFV threshold is set in step 52 based on the average or relative maximum AVFV at that point in time. If an AVFV which exceeds this threshold is not reached by the time the timer times out at step 54, then the presence of a VF is reconfirmed at step 56. If VF is still present, the defibrillation shock is delivered at step 58 synchronous with the next detected cardiac complex of the electrogram. If VF is not reconfirmed, then the shock is aborted at step 60. In the preferred embodiment, the timer is set for between about 2 and 6 seconds but a shorter or longer timer could be used. In the preferred embodiment, a running average of the AVFV is used at step 52 to set a threshold for delivery of the defibrillation shock. The average continues to be calculated even after capacitor charging is completed. In an alternative embodiment, an AVFV relative maximum is used to set the threshold at step 52. The value of the threshold must be set so that it is not so high that it is unlikely that an AVFV measured subsequent to completion of HV capacitor charging will be as large as the threshold AVFV but it must be sufficiently large that the benefit of the invention is realized. When the threshold is set based on a running average AVFV, a typical multiplier is between about 1.1 and 1.4. When the threshold is set based on a relative maximum AVFV, a typical multiplier for setting the threshold is between about 0.5 and 0.9.

Once the count down timer is started at step 50 a loop is started to find the appropriate time for delivery of the defibrillation shock. Since the running window continues across the time when the capacitors are fully charged, the defibrillation shock may be delivered at the first peak or trough following the charge completion if the AVFV threshold condition is met at step 62. Since the invention works best if the defibrillation shock is delivered synchronous with a relatively large peak, a second threshold is used to determine whether or not to deliver the defibrillation shock into a particular complex at step 64. This second threshold may be a function of the AVFV average or relative maximum value or may be independently set. If a sufficiently large peak is detected at step 64, then VF is reconfirmed at step 56 and the defibrillation shock is delivered at step 58. Depending on the duration of the running sequence of windows, the first threshold may be met and yet the most current cardiac complex be too small to satisfy the second threshold. This prevents delivering the defibrillation shock at a time when the number of excitable cells is greater than desired to benefit from the method of the invention. In that case, delivery of the shock is delayed for a period of a 250 msec window at step 66. Thus, the system will look at several peaks in the new window to find one which exceeds the second threshold. If one is not found within 250 msec, the AVFV from the latest window is used to calculate an updated average or relative maximum AVFV and set a new threshold at step 52.

FIG. 3 is a simulated recording of a far-field electrogram showing a ventricular fibrillation. Initially, the heart is in a sinus condition and then fibrillation occurs. Once the fibrillation is detected, which generally takes some minimum number of short cardiac intervals, charging of the high voltage capacitor of the defibrillator is initiated. At that time, the running sequence of windows is initiated. Depending on the fibrillation interval, each window will capture about 1 to 4 cardiac complexes. A longer window of up to one second or more could be used. The digitized fibrillation voltage signal is then processed to provide the AVFV for that window. The figure shows a defibrillation shock being delivered and the signal returning to a sinus condition.

In addition to the sensing electrode configuration shown in FIG. 1, which uses an RV pacing electrode to an active pulse generator case, far field sensing may be accomplished using electrograms from other combinations of electrodes, including those of FIGS. 4–9. Some electrode configurations may be better than others for determining the relative amount of depolarization of the heart, and the preferred configuration my be different for different patients. To determine the best configuration for a given patient, various combinations of the leads in a patient may be tested at implant to see which is most effective. Alteratively, the sensing configuration of the implantable defibrillator could be eternally programmable after implantation. The most effective configuration could be determined during post-operative testing.

Figure 4:
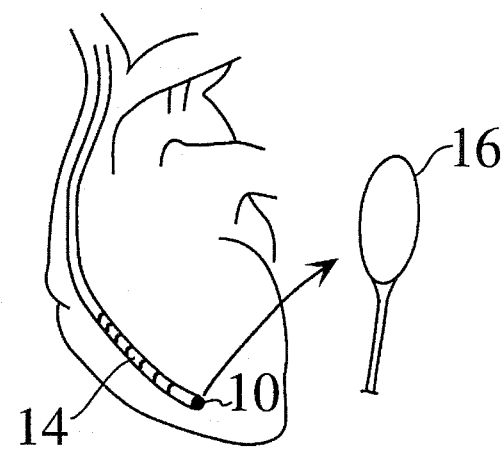
FIGS. 4–9 illustrate various sensing configurations for use with the invention.
Figure 5:
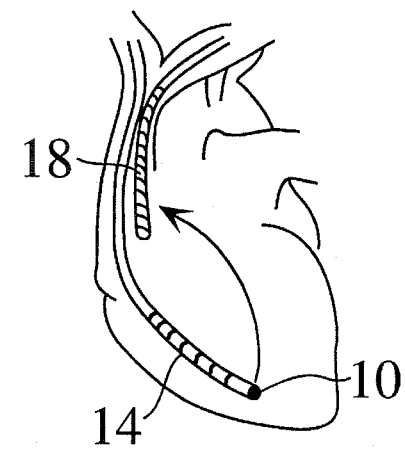
Figure 6:
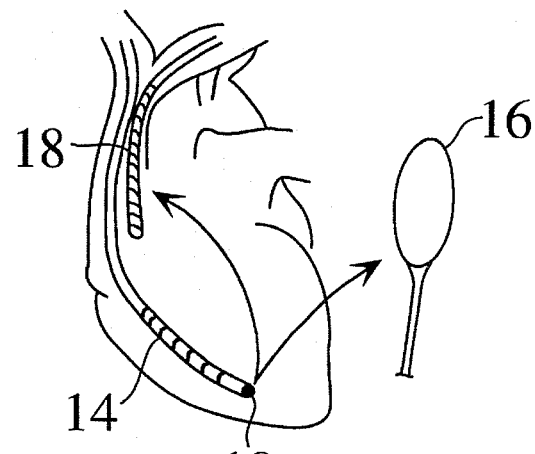

FIG. 4 is a schematic illustration of sensing the far-field ventricular electrogram using an RV pacing electrode 10 and a SubQ defibrillation electrode 16. This is the same configuration shown in FIG. 1, except that a separate SubQ defibrillation electrode 16 is used instead of an active pulse generator case 12. FIG. 5 is a schematic illustration of sensing the far-field ventricular electrogram using an RV pacing electrode 10 and an SVC defibrillation electrode 18. FIG. 6 is a schematic illustration of sensing the far-field ventricular electrogram using an RV pacing electrode 10, a superior vena cava (SVC) defibrillation electrode 18 and a SubQ defibrillation electrode 16. In this configuration, the RV pacing electrode acts as one pole, and the SVC and SubQ electrodes are taken in combination to form the second pole, so that only one far-field ventricular electrogram is produced.

In an alternative embodiment, the RV and SVC electrodes may form one sensing pair, and the RV and SubQ electrodes may form a second sensing pair, thus producing two far-field ventricular electrograms. In this way, additional information is obtained regarding the direction of the fibrillation wavefronts, and vectorcardiography may be used to further determine the period during which a defibrillation shock will be most likely to successfully terminate fibrillation.

Figure 9:
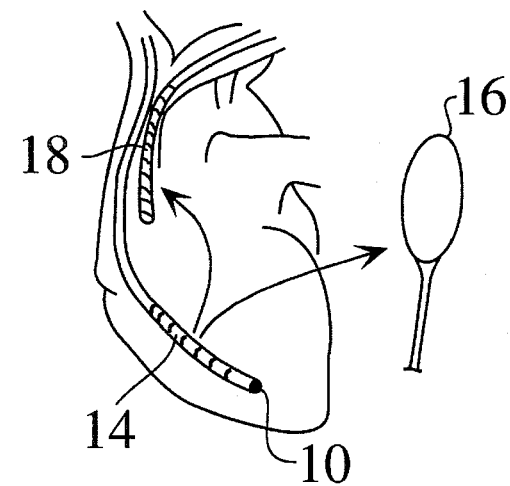

Two examples of utilizing two VF signals are shown in FIGS. 6 and 9. As shown in FIGS. 6 and 9, the sensing paths formed by the electrode pairs are approximately perpendicular to each other. In this way, when the fluctuation is great in both signals, the sum of their peak to peak envelope voltages will be greatest, representing the greatest level of organization in the heart. This in turn corresponds to the window of VF susceptible to defibrillation. To add an additional level of control to the timing of shock delivery, during this window just described, the exact moment of delivery may be timed with a relative maximum voltage from one of the signals or from the sum of the signals or from the sum of the rectified signals. Again, the optimum choice may be patient-dependent.

As another example of using the two fibrillation signals, instead of summing the envelope voltages, they can be compared to each other at each point in time, with only the larger peak to peak voltage stored. In this way, two medium peak to peak voltages would not have the same magnitude as one large and one small; the set with the one large signal would be considered to have a higher level of organization, and therefore be more susceptible to defibrillation. As before, the exact moment of energy delivery may be timed to coincide with a absolute VF voltage, this time using the signal with the large envelope voltage.

Figure 7:
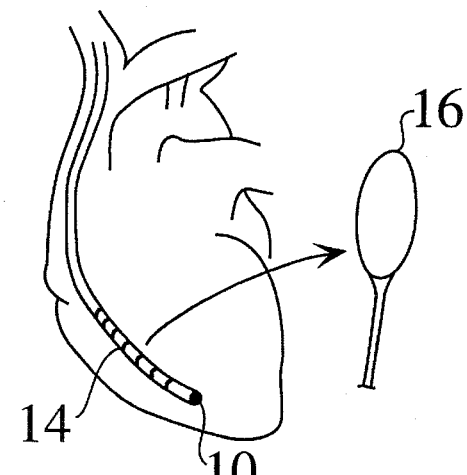
Figure 8:
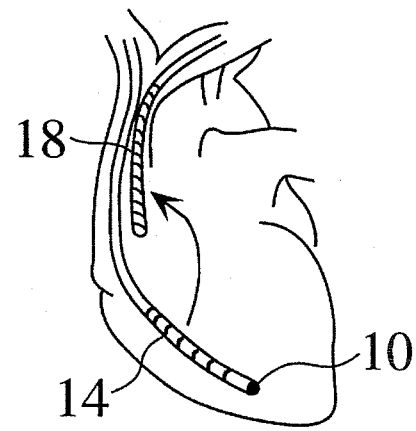

FIG. 7 is a schematic illustration of sensing the far-field ventricular electrogram using an RV defibrillation electrode 14 and a SubQ defibrillation electrode 16. FIG. 8 illustrates sensing the far-field ventricular electrogram using an RV defibrillation electrode 14 and an SVC defibrillation electrode 18.

FIG. 9 is a schematic illustration of sensing the far-field ventricular electrogram using an RV defibrillation electrode 14, an SVC defibrillation electrode 18 and a SubQ defibrillation electrode 16. As described with reference to FIG. 6, the RV electrode may be used with the SVC and SubQ electrodes either in combination or separately to form one combined or two separate ventricular electrograms. It is noted that an active pulse generator case may be used for the SubQ electrode in each of the embodiments shown in FIGS. 4, 6, 7 and 9.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A method for defibrillating a patient's heart with an implantable defibrillator having first and second implanted electrodes spaced apart from each other by at least 4 centimeters, comprising the steps of:

(a) detecting fibrillation in said patient's heart;

(b) monitoring a fibrillation voltage across said first and second implanted electrodes, a waveform of said fibrillation voltage including peaks and troughs;

(c) determining absolute value amplitudes of the peaks and troughs of said fibrillation voltage;

(d) averaging a portion of said absolute value amplitudes to provide an average amplitude;

(e) comparing said average amplitude with the absolute values of the peaks and troughs of said fibrillation voltage to determine if a measure of the absolute values of the peaks and troughs of said fibrillation voltage exceeds said average amplitude determined in step (d) by a predetermined amount; and (f) delivering a defibrillation shock to said patient's heart during a period of ventricular fibrillation when the measure of the absolute values of the peaks and troughs of said fibrillation voltage exceeds said average amplitude determined in step (d) by said predetermined amount.

2. The method of claim 1 wherein said step of delivering said defibrillation shock includes delivering said shock synchronous with a peak or trough of said fibrillation voltage having an amplitude exceeding a threshold set as a function of said average amplitude.

3. The method of claim 1, wherein said implantable defibrillator includes a third electrode and wherein said step (a) of detecting fibrillation includes the step of sensing an electrical signal from said patient's heart with said first and third electrodes.

4. The method of claim 1, wherein step (f) of delivering a defibrillation shock includes the step of delivering said defibrillation shock using at least one of said first and second spaced apart electrodes used to monitor said fibrillation voltage in step (b).

5. The method of claim 1, and further including the step of implanting said first and second spaced apart electrodes for monitoring fibrillation respectively in the right ventricle of said patient's heart and in a subcutaneous pectoral region.

6. The method of claim 1, wherein said implantable defibrillator includes a third implanted spaced apart electrode and wherein step (b) includes monitoring a first and a second of said fibrillation voltages, said first and second spaced apart electrodes forming a first electrode pair for monitoring said first fibrillation voltage, and said first and third spaced apart electrodes forming a second electrode pair for monitoring said second fibrillation voltage.

7. The method of claim 1, and further including the steps of charging a high voltage capacitor in said implantable defibrillator following detection of fibrillation in said patient's heart and of setting a safety timer upon completion of said charging step and delivering said defibrillation shock when said safety timer times out if said measure of the absolute values of the peaks and troughs of said fibrillation voltage has not exceeded said average amplitude by said predetermined amount.

8. The method of claim 1 wherein said step of averaging a portion of said absolute value amplitudes includes sequentially calculating the average using a running sequence of windows, each window including a defined time duration of said fibrillation voltage, whereby newer windows are included in said averaging and older windows are excluded from said averaging.

9. An implantable defibrillator comprising:

(a) a pulse generator including a battery, a high voltage capacitor and a charging circuit for charging said capacitor from said battery;

(b) bipolar fibrillation sensing means;

(c) unipolar sensing means for monitoring a fibrillation voltage and determining a relative measure of the strength of peaks and troughs of said fibrillation voltage measured during a running sequence of windows monitored following fibrillation detection;

(d) electrode means for delivering a defibrillation shock from said capacitor, during a period of ventricular fibrillation after said capacitor is charged when a measure of the absolute values of the peaks and troughs of said fibrillation voltage exceeds by a predetermined percentage said relative measure;

wherein said unipolar sensing means comprises at least two of the following:

(aa) a right ventricular pacing electrode;
(bb) a subcutaneous defibrillation electrode;
(cc) an electrically active portion of the implantable defibrillator case;
(dd) a superior vena cava defibrillation electrode;
(ee) a right ventricular defibrillation electrode.

10. The implantable defibrillator of claim 9 wherein said unipolar sensing means comprises at least three electrodes.

11. The implantable defibrillator of claim 9, wherein said unipolar sensing means comprises a first electrode and a second electrode, and wherein said electrode means for delivering a defibrillation shock includes said first electrode.

12. The implantable defibrillator of claim 11, wherein said electrode means for delivering a defibrillation shock further includes said second electrode.

13. A method for defibrillating a patient's heart with an implantable defibrillator having first and second implanted electrodes spaced apart from each other by at least 4 centimeters, comprising the steps of:

(a) detecting fibrillation in said patient's heart;

(b) monitoring a fibrillation voltage across said first and second implanted electrodes, a waveform of said fibrillation voltage including peaks and troughs;

(c) determining absolute value amplitudes of the peaks and troughs of said fibrillation voltage;

(d) calculating a measure of said amplitudes for a sequence of predefined duration portions of said fibrillation voltage;

(e) calculating an average of said measures for a predetermined number of said portions;

(f) comparing said average measure with at least one of said measures for one of said portions in said sequence subsequent to said predetermined number of said portions to determine if said measure for said subsequent portion exceeds said average measure calculated in step (e) by a predetermined amount; and (g) delivering a defibrillation shock to said patient's heart during a period of ventricular fibrillation when said measure for said subsequent portion exceeds said average measure by said predetermined amount.

14. The method of claim 13 wherein step (d) includes adding said amplitudes for each predefined duration portion to calculate each of said measures.

15. The method of claim 13 wherein step (d) includes averaging said amplitudes for each predefined duration portion to calculate each of said measures.

* * * * *